United States Patent [19]

Ralph et al.

[11] Patent Number: 4,730,036

[45] Date of Patent: Mar. 8, 1988

[54] PURIFICATIONS OF B-CELL INDUCING FACTOR (BIF) AND B-CELL GROWTH FACTOR (BGF)

[75] Inventors: Peter Ralph, Purdys; Karl Welte, New York, both of N.Y.

[73] Assignee: Sloan-Kettering Institute for Cancer Research, New York, N.Y.

[21] Appl. No.: 567,562

[22] Filed: Jan. 3, 1984

[51] Int. Cl.$^4$ .................... C07K 3/20; C12P 21/00; C12N 5/00

[52] U.S. Cl. .................... 530/351; 435/7; 435/68; 435/240.27; 530/412; 530/416; 530/417

[58] Field of Search .................. 435/7, 68, 240; 530/412, 416, 417, 351

[56] References Cited

U.S. PATENT DOCUMENTS

| | | | |
|---|---|---|---|
| 4,596,774 | 6/1986 | Chang | 530/351 X |
| 4,613,459 | 9/1986 | Cantor | 530/351 |
| 4,624,917 | 11/1986 | Sugimoto | 530/351 X |
| 4,661,447 | 4/1987 | Fabricius | 530/351 X |
| 4,675,383 | 6/1987 | Bohlen | 530/351 |

OTHER PUBLICATIONS

Teranishi, T. et al., J. Immunol., 128(4), 1903–1908 (1982).
Falkoff, R. J. M. et al., J. Immunol., 129(1), 97–102 (1982).
Yoshizaki, K. et al., J. Immunol., 128(3), 1296–1301 (1982).
Muraguchi, A. et al., J. Immunol., 129(3), 1104–1107 (1982).
Ralph, P. et al., J. Immunol., 132(4), 1858–1862 (1984).

*Primary Examiner*—Sidney Marantz
*Attorney, Agent, or Firm*—John P. White

[57] ABSTRACT

Highly purified T cell replacing factor (TRF or BIF) essentially free of IL-2 and Interferon activities is obtained in the invention. BIF is useful for treatment of immunoregulatory disorders and/or stimulation of production of immunoglobulins. A method for production of BIF and BGF is described.

B cell lines for BIF assays are described as well as an assay for B cell receptor variants and a method for obtaining B cell variants from a variety of source materials.

15 Claims, No Drawings

PURIFICATIONS OF B-CELL INDUCING FACTOR (BIF) AND B-CELL GROWTH FACTOR (BGF)

The present invention was partially made with funds provided from the National Institutes of Health, grants CA-20194 and AI15811 and USPHS grants CA-24300, CA-19052. Therefore the U.S. Government may have certain rights in this invention.

This invention relates to B cell inducing factor (BIF), B-cell growth factor (BGF) and immunoregulatory systems. A method for purification of BIF and BGF and a method for assay of BIF are presented.

BACKGROUND

The history of BIF involves the maturational development and history of B lymphocytes (B cells) of the immunoregulatory system. B cells originate from hematopoietic stem cells and then B cells differentiate into memory cells and plasma cells. It is the plasma cells which secrete immunoglobulin. These transformations are regulated by humoral and cellular factors. Certain human B-lymphocyte cell lines in long-term culture can be stimulated to produce IgM or IgG by co-culture with normal allogeneic T-lymphocytes, by incubation with lymphokine (LK) preparations and by incubation with tumor promoter phorbol myristic acetate (PMA). The presence of T-cell signals were found to be necessary for B cells to mature to immunoglobulin-secreting cells (ISC). One such signal is BIF. BIF has also been known as helper factor, T-cell replacing factor (TRF) and B cells differentiation factor (BDF).

Secretion of antibody is initiated by the binding of antigen to immunoglobulin receptors on the B-lymphocyte surface, together with help from subsets of T cells and accessory cells. This process involves expansion (proliferation) of the triggered B cells and differentiation into plasmacytes, or immunoglobulin-secreting cells (ISC). For many in vitro systems using human lymphocytes, the requirement for helper T cells in induction of B cells can be largely replaced by lymphokines, including growth factors (Muraguchi, et al. (1983) J. Exp. Med. 157: 530; Maizel, et al. (1982) Proc. Nat'l. Acad. Sci. U.S.A. 79: 5998; Okada, et al. (1983) J. Exp. Med. 157: 583) and/or differentiation factors (Insel, et al. (1977) J. Immunol. 118: 2009; Hirano, et al. (1977) J. Immunol. 119: 1235).

A model system for inducing large numbers of human ISC uses the polyclonal activator *Staphylococcus aureus* strain Cowan I (Sac). The killed bacteria are a potent B-cell mitogen and were originally described as inducing immunoglobulin secretion in the absence of T cells (Ringdon, et al. (1977) Scand. J. Immunol. 6: 1159; Pryjima, et al. (1980) J. Immunol. 124: 656; Dosch, et al. (1980) J. Immunol. 125: 827). Saiki, et al. (1981) (J. Immunol. 127: 1044) confirm that Sac is a T-independent mitogen (DNA synthesis) for peripheral blood B cells, but Saiki, et al. (1981) Supra, and Saiki, et al. (1982) (Cell. Immunol. 70: 301) and others (Falkoff, et al. (1982) J. Immunol., 129: 97) find that Sac is very dependent on T cells for induction of ISC. Sac appears to trigger B cells via an interaction of the bacterial protein A with the antigen-binding (Fab) regions of immunoglobulin receptors, at least in the case of IgM-bearing cells (Romagnani, et al. (1982) J. Immunol. 129: 596).

Since B cells are stimulated by Sac to a high degree of proliferation but seem to require T cells or lymphokine for immunoglobulin secretion, this is an excellent system for the assay of B-cell inducing factor (BIF) which specifically recruits cells into secretion. This invention concerns the purification of BIF for IgM, IgG and IgA production in human blood cells and its relation to interleukin 2 (IL-2).

Human B-lymphocyte lines in long-term culture are models for normal B-cell differentiation. Stimulation of cell line IgM and IgG secretion by coculture with normal allogeneic T lymphocytes (Kishimoto, et al. (1978) Nature (London) 271: 756; Kempner, et al. (1980) Cell Immunol. 55: 32), by incubation with lymphokine preparations (Muraguchi, et al. (1981) J. Immunol. 127: 412; Teranishi, et al. (1982) J. Immunol. 128: 1903; Saiki, et al. Eur. J. Immunol. (1983) 13: 31), and by incubation with tumor promoter phorbol myristic acetate (PMA) (Ralph, et al. (1981) J. Clin. Invest. 68: 1093) have been reported. Human B-cell-inducing factors (BIF) which induce immunoglobulin-secreting cells (ISC) are produced by T lymphocytes in response to mitogens (Hirano, et al. Supra (1977); Saiki, et al. Supra (1981)), allogeneic cells (Friedman, et al. (1979) J. Immunol. 122: 1302), and antigen (Geha, et al. (1973) J. Exp. Med. 138: 1230). T-Cell hybridomas also appear to secrete BIF (Okada, et al. (1981) Proc. Nat'l. Acad. Sci. U.S.A. 78: 7717). With the demonstration that PMA can induce BIF in cultures of peripheral blood T cells (Ralph, et al. (1981) Clin. Immunol. Immunopathol, 22: 340), it became important to determine that the direct stimulatory effect of PMA on ISC formation in B-cell lines was related to the action of BIF (Maurer et al. Cell. Immunol. (1982) 79: 36).

SUMMARY

Highly purified T cell replacing factor (TRF or BIF) essentially free of IL-2 and interferon activities is obtained in the invention. BIF is useful for treatment of immunoregulatory disorders and/or stimulation of production of immunoglobulins. A method for production of BIF and BGF is described.

B cell lines for BIF assays are described as well as an assay for B cell receptor variants, and a method for obtaining B cell variants from a variety of source materials.

A cell line assay has been established for IgM-BIF and cell lines positive and negative for receptors for this activity are described (Saiki, et al. (1983) Eur. J. Immunol. Supra).

An IgG cell is found which is greatly stimulated by PMA and lymphokine (LK) to generate ISC. It is shown that PMA and BIF act synergistically on the IgG line ARH-77 and suggest that IgM- and IgG-BIF may be separate factors (Maurer, et al. (1983) Supra).

DESCRIPTION

Purification of BIF

Preparation of Ly-CM(I): Lymphokine (LK) as starting material was prepared from normal peripheral blood mononuclear cells by stimulation of said cells with 1% phytohaemagglutinin (PHA). If the source is human mononuclear cells from uninvolved spleen sections of Hodgkin's disease patients, these are purified by flotation on F. Coll-Hypaque (Ralph, et al. (1981) Clin. Immunol. Immunopathol. 22: 340). Spleen cells were cultured at $2 \times 10^6$ ml MEM alpha plus 0.2% fetal calf serum (FCS), 0.5% PHA and 10 ng/ml PMA for 48 hrs. Control conditioned medium was prepared by incubating spleen cells 47 hrs. with PHA and PMA added 1 hr before harvesting. For lymphokine prepared from peripheral blood mononuclear cells stimulated with 1% PHA (DIFCO Laboratories, Detroit, Mich.) for $4 \times 10^6$ cells/ml in RPMI 1640 medium containing 0.25% bovine serum albumin (Sigma, St. Louis Mo.) is used as described (Welte, et al. (1982) J. Exp. Med. 156: 454). The cells are incubated at 37° C. for 48 hrs, after which cells and cell debris are removed from the lymphocyte conditioned-medium (Ly-CM) by centrifugation at 10,000 g for 15 min). Other stimulators such as Pokeweed mitogen (PWM), Concanavalin (Con A) and allogeneic T-cells can be used. The Ly-CM, containing lymphokines, is used for purification of BIF. Partially purified, delectinized lymphokines produced by PHA-stimulated blood cells are purchased from Folex-Biotest-Schleussner Inc. Fairfield, N.J. (Lymphocult-T-LT) and Electro-Nucleonics Silver Spring, Md. Other lymphocyte sources such as tonsile tissue may be used as well; also any hematopoietic material which will yield lymphocytes.

Ammonium Sulfate precipitation (II)

BIF and IL-2 co-purify through a number of steps of a previous scheme (Welte, et al. (1982) J. Exp. Med. 156: 454). Proteins including lymphokine material are precipitated from Ly-CM which is 80% saturated with $(NH_4)_2SO_4$. (e.g. 1683 g $(NH_4)_2SO_4$ is added to 3 liters of Ly-CM). The mixture is stirred overnight at 4° C., the precipitate is spun down at 10,000 g for 15 min and dissolved in 0.05M Tris-HCl at pH 7.8 in a final volume of 300 ml. This volume is dialyzed against 50 volumes of 0.05M Tris-Hcl buffer pH 7.8 for 48 hrs with 5 changes of the dialyzing buffer over that period of time.

Anion Exchange chromatography (III)

The dialyzed material from the step above is applied to a 200 ml column of DEAE-cellulose (DE-52, Whatman Laboratory, Clifton, NJ). Protein is batch-eluted at 0.1M, 0.3M and 0.5M Nacl, 0.05M Tris-Hcl, pH 7.8. Lymphokine not binding to DE-52 at 0.1M Nacl was collected and concentrated by dialyzing against Tris-HCl (see above) containing 50% polyethyleneglycol (w/v) PEG6000).

Size fractionation (IV)

The concentrated 0.1M NaCl eluant above is size fractionated on an ACA 44 Ultrogel column (LKB products, Rockland, Md, $2.5 \times 90$ cm) developed with phosphate buffered saline (PBS), pH 7.3 containing 0.1% w/v polyethylene glycol (PEG 6,000) to stabilize proteins. The column was calibrated with bovine serum albumin (m.w. 68,000), chymotrypsinogen (M.W. 25,000) and ribonuclease A (m.w. 14,000) (Pharmacia, Piscataway, N.J.). The flow is about 30 ml/hr and 6 ml fractions are collected. Proteins of between 15–25,000 apparent molecular mass $(M_R)$ were pooled.

Agarose chromatography a. Blue agarose (V):

The pooled Ultrogel fractions above (45–60) were applied to a blue agarose column (BRL, Gaithersburg, Md) with a bed volume of 40 ml, previously equilibrated with PBS.

Fractions were eluted with 0.1M increments of PBS (0.3–1M). High Salt eluates were pooled and dialyzed against PBS. IL-2 is generally found in 0.8M NaCl fractions while BIF and BGF are found in 0.3–0.5M NaCl fractions if they separate out (dependent on Ly-CM batch).

b. red agarose chromatography (VI):

The blue agarose eluates with BIF activity were loaded on a 10 ml Procion-red agarose (BRL) column equilibrated with PBS. The column is washed with PBS and bound proteins are eluted with stepwise (0.3, 0.5, 1.0) increments in a 0.3M-1.0M gradient of PBS. High salt eluates (0.5–1.0M NaCl) containing both Interleukin-2 (IL-2) and BIF were collected. IL-2 is generally found in 1.0M NaCl fractions while BIF and BGF are found in 0.3–0.5M NaCl if they separate out (dependent on LY-CM batch).

High Pressure Liquid Chromatography (HPLC) (VIII)

The high salt eluates from red agarose above are fractionated by reverse phase HPLC on a Protesil 300 column (Whatman) using a linear gradient of 1-propanol in 1% phosphoric acid-triethylamnine (TEAP) pH 3.0, at about 0.5 ml/min, BIF activity is found at about 35% propanol/TEAP whereas IL-2 activity is located at about 40%. One-half of each fraction was immediately stabilized by addition of 10 microgram/ml of BSA with dialysis against PBS.

Fractions from HPLC above were assayed for protein concentration, stabilized with albumin, dialyzed and assayed for IL-2 and BIF. Protein was estimated by Bio-Rad Protein Assay (microassay procedure using bovine albumin as a standard).

Standard BIF

Partially purified, delectinized lymphokines produced by PHA-stimulated human blood cells were used as BIF standards for the assays performed below. These lymphokine standards were purchased from Folex-Biotest-Schleussner, Inc., Fairfield, NJ (lymphocult-T-LF) and Electro-Nucleonics Laboratories, Silver Spring, Md.

BIF Assay on normal B cells by ISC induction in SAC stimulated B cells

B cells (plus monocytes and null cells) were obtained from normal adult volunteers by centrifugation of heparinized venus blood on Ficoll-Hypaque followed by two cycles of rosetting with neuraminidase-treated sheep erythrocytes to remove T cells (Saiki, O. et al. (1982) cell Immunol. 129: 97). These preparations contain less than 1% T cells and had no immunoglobulin secreting cells (ISC) response to pokeweed mitogen (PWM, GIBCO Laboratories, Grand Island, NY) (see Table I). B cells were cultured at $10^5$ cells per 0.2 ml alpha MEM medium with 10% fetal bovine serum, plus 0.001% v/v *Staphylococcus aureus* strain Cowan I (Sac) (Pansorbin 10% v/v, Calbiochem-Behring Corp., San Diego, CA) as described (Saiki, Supra).

BIF preparations were assayed by addition of 20 microliter dilutions and ISC were scored at day 6 or 7. ISC were detected by reverse plaque assay (Gronowicz, E. et al. (1976) Eur. J. Immunol. 6: 558) using protein A-coated sheep erythrocytes and polyvalent rabbit anti-immunoglobulin developing antiserum (Cappel Laboratories, Cochranville, PA). Class-specific ISC were detected by using rabbit anti-IgM, anti-IgG (Calbiochem-Behring) or anti-IgA (DAKO, Accurate Chemical & Scientific Corp., Hicksville, NY) as described previously (Saiki, Supra, Ralph, et al. (1981), J. Clin. Invest. 68: 1093, Maurer et al. (1983) Cell. Immunol. 79: 36).

The BIF concentration in a sample was defined by the dilution giving half maximal stimulation compared to a standard preparation: activity units/20 microliter dilution at half maximum. Controls measured the number of ISC in B cell cultures with SAC alone and this number was substracted from experimental values. For example, partially purified LK (lymphocult-T, Bio-test and 1:3 and 1:10 dilutions were assayed for BIF as above. Sac alone gives 60 ISC/2×10⁴ cells, Sac plus undiluted LK gave plateau levels of 902 ISC; half maximal stimulation $$\left[ \frac{902 - 60 = 421 \, ISC}{2} \right]$$

occurred at a dilution of 16.1 and the titer was 16.1/20 microliter=805 U BIF/ml. Dilutions of 1:3 and 1:10 had titers of 375 and 74 U BIF/ml respectively. In like manner fractions from ion exchange, affinity and high pressure liquid chromatographies were analyzed during the purification process. This method was used to determine BIF units activity. Thus after HPLC BIF activity is about 154,000 U/Mg protein.

BIF assay on B-cell lines

Assay methods for BIF also involve human B cell lines ARH-77 and SKW 6.4. These are discovered to be especially BIF-sensitive cell lines. ARH-77 is a B cell line containing Epstein-Barr virus. This line has been previously described (Ralph, P., et al. (1981) J. Clin. Invest., 68: 1093 and Ralph, P. (1979) Immunol. Revs. 48: 107). Cultures are grown in MEM alpha medium (Microbiological associates, Walkersville, Md.) supplemented with 100 units penicillin and 100 microgram streptomycin/ml and 10% fetal calf serum.

SKW6 Cell line cultures

SKW6 is an Epstein Barr virus-positive culture of the B cell line DAUDI described previously (Kishimoto, et al. (1978) Nature 271: 756). Cells (10⁴) were cultured in flat-bottom microtiter plates (3040, Falcon Plastic, Oxnard, CA) with each microwell containing 0.2 ml of culture medium. Culture medium was MEM alpha medium (Gibco, Grand Island, NY) supplemented with 100 U pencillin/ml, 100 microgram streptomycin/ml, 0.2 mg L-glutamine, and 10% fetal calf serum (Sterile Systems, Logan, UT). AT the end of incubation, cells were washed and resuspended in Hank's balanced salt solution (HBSS) for assay. Papers on this work are hereby incorporated by reference (Ralph, et al. (1983) Immunology Letters 7: 17 in Press, Saiki, et al. Eur. J. Immunology (1983) 13: 31 and Maurer, et al. Cell. Immunol. (1983) 79: 36).

Cloning

Cells were cloned by limiting dilution. Briefly, a total of 30 cells were cultured in 96-well flat-bottom microtiter plate (one cell/every three wells). As feeder cells, 10⁵ normal mouse adherent peritoneal cells were put in wells 1 day before cloning. At day 10, plates were carefully examined by microscopy and growing cells were harvested and transferred to another plate. By this method usually about 10 clones were generated from each plate.

IL-2 Assay

IL-2 was assayed on the IL-2 dependent murine T cell line CTLL by ³H dT incorporation (Welte, et al. (1982) J. Exp. Med. 156: 454). In some experiments, a murine IgA monoclonal antibody which neutralizes the activity of IL-2 was used. (Mertelsman, et al. (1983) in Normal and Neoplastic Hematopoiesis, P.A. Marks, editor. Academic Press, NY in press).

Induction of ISC by PMA or LK

Cell lines were incubated at 0.8 to 2×10⁵/ml in petri dishes (1008, Falcon Plastics, Oxnard, Calif.) or microwells (3040, Falcon). After various times the cells were harvested, washed, and assayed for ISC.

Plaque-forming cell assay for immunoglobulin secretion. The method of reverse plaques on protein A-coated sheet red blood cells was used with class-specific developing antisera to detect ISC exactly as described previously (Saiki, et al. Eur. J. Immunol. (1983) 13: 31; Ralph, et al. J. Clin. Invest. (1981) 68: 1093; and Saiki, et al. J. Immunol. (1981) 127: 1044).

ARH-77 Cell line culture

ARH-77 was described (Ralph, et al. (1981) J. Clin. Invest. 68: 1093 and Ralph, P., et al. (1979) Immunol. Res. 48: 107) and is presumably derived from normal B cells since it contains Epstein-Barr virus (EBNA positive, G. Klein and K. Nilson, personal communication). Cultures were grown in MEM alpha medium (Microbiological Associates, Walkersville, MD) supplemented with 100 units/ml penicillin and 100 micrograms streptomycin/ml and 10% fetal calf serum.

Mitogens

PMA was from Sigma Chemical Company (St. Louis, MO) and Consolidated Midland, Brewster, N.Y.). Phytohemagglutinin (PHA-M) was from GIBCO (Grand Island, N.Y.).

Assay for B-cell Inducing Factor (BIF)

Factors inducing immunoglobulin secretion were assayed on peripheral blood B cells stimulated into DNA synthesis by killed Staphylococcus bacteria (Saiki, et al. Supra (1981) J. Immunol.). T lymphocytes were depleted from blood mononuclear cells by two cycles of rosetting with neuraminidase-treated erythrocytes and Ficoll-Hypaque centrifugation to obtain a B-cell plus monocyte preparation which contained less than 1% T cells and usually had no pokeweed mitogen (PWM) response (Saiki, et al. (1982) Cell. Immunol. In the initial studies immunoglobulin secreting cells (ISC) of IgM, IgG or IgA class were detected in a reverse plaque assay using a polyvalent developing antiserum. In 22 experiments with B cells of 9 normal donors there was a median value of 900 ISC per 2×10⁴ initial cells using Sac plus optimum concentrations of BIF (Table I). In 21 of the 22 experiments ISC with Sac only was less than 20% of maximum ISC using Sac plus BIF. The response of the B cells to Sac plus PWM, a most sensitive functional test for the presence of T helper cells (Saiki, et al. (1982) Supra), was also less than 20% of that to Sac plus BIF in most of the experiments. These two criteria were used for all the experimental data reported hereafter.

The concentration of BIF in different preparations was defined by the dilution giving half maximum numbers of ISC compared to a standard preparation. Thus, an undiluted preparation which stimulates half maximum numbers of ISC at the assay volume of 20 microliters was arbitrarily assigned to a value of 500 units/ml (1 U/20 microliter). 3- and 10-fold dilutions of a standard preparation titered at 3.2-fold and 10.9-fold lower than the original.

Unfractionated lymphokines and BIF preparations after the first two steps of purification (ammonium sulfate precipitation and ion exchange chromatography) often contained a high molecular weight inhibitor which made it impossible to determine the exact concentration of BIF until further purification which would remove the inhibitor. Examples of BIF titrations are given in Table II.

Purification of BIF

BIF was enriched according to the scheme used for purification of IL-2 (Welte, et al. (1982) J. Exp. Med. 156: 454 and Ralph, et al. (1984) J. Immunol. in Press which is hereby incorporated by reference; see above). LK proteins were precipitated in 80% ammonium sulfate and applied to a DEAE cellulose column. BIF passed through the column in the 0.1M Nacl, pH 7.8 starting buffer, together with all the IL-2 activity, whereas most of the protein bound to the column (Table II). A small amount of BIF activity eluted with 0.5M NaCl and this was not fractionated further. The material passing through the ion exchange column was size fractionated on an AcA 44 column. This shows that BIF which induces ISC in Sac-stimulated B cells eluted with an apparent molecular weight of about 20,000 and partially overlapped with IL-2.

The gel filtration step did not increase the specific activity of BIF in the pooled peak fractions, but did remove a high molecular weight inhibitor of the assay. The possibility that some high molecular weight fractions contain BIF activity which is masked by inhibitors is currently being investigated.

The size fractions with BIF activity (approximately 20K) were pooled and subjected to affinity chromatography on blue agarose. Most of the protein passed through the column, but BIF bound and was eluted at high salt with some fractions free of IL-2 activity. Since IL-2 is being routinely purified in this laboratory for clinical trials (Mertelsman, et al. in Normal and Neoplastic Hematopoiesis P. A. Marks, editor Academic Press, NY in press), further purification of BIF was obtained as a by product. High salt eluates from blue agarose which contained both IL-2 and BIF were pooled, applied to a red agarose column which bound both activities but not most of the remaining protein including alpha and gamma interferon (Welte (1982) Supra), and the high salt eluate from red agarose was subjected to reverse phase HPLC. BIF elutes at about 35% propanol in HPLC as a major peak and a minor fraction well separated from IL-2. The specific activity at this stage, Fraction VII, was about 154,000 U/mg protein, representing an 11,000-fold purification (Table II). With some lots of Ly-CM, there is some separation of IL-2 and BIF after agarose chromatography.

BIF for Induction of IgM, IgG and IgA Production

BIFs which induced IgM, IgG and IgA-ISC copurified throughout these procedures, assayed by using class-specific antisera to develop plaques. Thus, unfractionated lymphokine, the DE-52 fractions of 0.1M and 0.5M NaCl, the 20,000 $M_r$ size fraction, and blue agarose-purified BIF which was free of IL-2 induced IgM, IgG and IgA-ISC in similar ratios (Table III). IgG and IgA-ISC were 50–170% and 20–60% of IgM-ISC, respectively, depending on the donor cells assayed.

BIF Effect is Independent of IL-2

Table IV shows that purified IL-2 has no BIF activity, that IL-2 does not enhance the activity of BIF, and that a monoclonal antibody to IL-2 does not affect induction of ISC by BIF. B cells cultured with Sac with or without BIF do not produce detectable IL-2 (less than 0.2 U/ml). Thus, IL-2 does not seem to play a role in this assay system.

We have used an assay for BIF which depends on Sac stimulation of peripheral blood B lymphoctyes depleted of T cells (Saiki, et al. (1981) J. Immunol. Supra and Saiki, et al. (1982) Cell. Immunol. Supra). This is a potent assay system since BIF-induced ISC amounts to an average of 5% of initial cells cultured using a number of normal donors (Table I). The procedure presented in this invention for purification of BIF introduces batch chromatography on blue agarose and red agarose. The binding of BIF to these dyes is likely a result of electrostatis and/or hydrophobic interactions. The use of these two steps and HPLC permitted and 11,000-fold purification of BIF. Other purification methods for similar factors which do not depend on specific antigen stimulation have a much lower apparant specific activity. These include human factors assayed using human B cell lines infected with Epstein-Barr virus (Teranishi, et al. J. Immunol. (1982) 128: 1903 and Yoshizaki, et al. (1982) J. Immunol. 128: 1296) and murine factors (Pure, et al. (1983) J. Exp. Med. 157: 600). Our purification procedure also avoided time-consuming steps, making it convenient for large-scale purification of BIF. Isolelectric focussing and CMC columns were also tested for purification of BIF. No BIF activity could be recovered in two experiments of isoelectric focussing, although IL-2 could be fractionated by this procedure (Welte (1982) Supra). BIF eluted at slightly higher salt concentration (about 0.3M NaCl) than IL-2 on a CMC column, but the two activities overlapped.

In the present purification scheme (Table II) the overall yield of BIF was about 1%. This low yield may be due in part to following the purification steps for IL-2. IL-2 in high concentrations can be assayed directly by dilution from high salt of the HPLC propanol buffer. For BIF assays, prior dialysis was necessary which may have led to loss of activity. In low protein concentrations BIF also appears to be more labile to propanol-acid pH (90% activity loss in 24 hr at 4° C.) than IL-2 (essentially stable under the same conditions). In addition to losses due to possible denaturation, some BIF elutes at 0.5M NaCl from DEAE cellulose and is discarded (Table II), and some activity may be of high $M_r$ and be masked by inhibitors.

Size fractionation of lymphokines which stimulate immunoglobulin secretion in human B cell lines show a low $M_r$ component (about 20K) for IgM line SKW6.4 (Maurer, et al. (1983) Cellular Immunol. 79: 36) and for three IgG lines (Maurer, et al. (1983) Supra, Teranishi, et al, (1982) Supra, Yoshizaki, et al. (1982) J. Immunol. 128: 1296). In addition, material of 30–60,000 $M_r$ stimulates immunoglobulin secretion by the IgG lines (Maurer, et al. (1983) Cell. Immunol., teranishi, et al. (1982) Supra) but not by the IgM line (Maurer Supra (1983). These cell line studies may not represent true induction of ISC since the cultures have low numbers of secreting cells initially, even after repeated cloning. The failure to find a high $M_r$ BIF for IgG secretion by blood cells in the present experiments has several interpretations: (1) B cells sensitive to the high $M_r$ BIF may belong to a subset not found in blood. However, we find that spleen cells give very similar numbers of IgM, IgG and IgA-ISC as blood cells in assays of size fractions with no evidence of a high Mr inducing factor. (2) the IgG cell lines may not be sensitive to inhibitors which mask BIF activity, in contrast to the IgM line and normal donor B cells. Current studies on the inhibitor may clarify this point. (3) Cell lines receptive to BIF may be in a different physiological state from normal B cells stimulated by Sac, and a different initial stimulus to the normal population may render them receptive to the high $M_r$ factor.

BIFs for induction of IgM, IgG and IgA-ISC copurified through Fraction V in the biochemical procedures (Table III). On the other hand, there is evidence for separate factors for IgM and IgG production in mice (Pure, et al. (1983) J. Exp. Med. 157: 600). Human (Mayer, et al. (1982) J. Exp. Med. 156: 1860; Endoh, et al. (1981) J. Immunol. 127: 2612) and murine (Kyono, et al. (1982) J. Exp. Med. 156: 1115; Kawaniski, et al. (1983) J. Exp. Med. 157: 433) T cells which specifically induce IgA production have also been described. Thus, further purification of our factor may disclose isotype-specific activities. The B cells in human blood which are induced to secrete IgG or IgA by Sac plus T cells by PWM plus T cells, or by the synergistic combination of Sac plus PWM plus T cells appear to be memory cells, largely IgM⁻ and IgD⁻ (Saiki, et al. (1982) Eur. J. Immunol. 12: 506; Kuratani, et al. (1982) J. Exp. Med. 155: 1561). Therefore, Sac plus purified BIF may trigger memory B cells or cells recently stimulated in vivo to secrete regardless of isotype. However, Fraction V BIF also induces high numbers of IgG- and IgA-ISC in splenic B cells, which appear to be virgin cells (largely surface IgM⁺, IgD⁺, Saiki, et al. (1982) Clin. Immunol. Immunopathol. 25: 114). We believe that BIF material described herein is an inducer of all classes of ISC, but the question of whether it also induces class switching in spleen populations is open.

It is important to distinguish IL-2 from BIF. IL-2 is a major component of the BIF-containing fractions through much of the purification steps. Separation of the two factors can be achieved by analytical chromatography on size (ultrogel) or affinity (agarose) columns, but in low yields due to the partially overlapping elution profiles. In this purification scheme BIF is easily separated from IL-2 by HPLC. On HPLC BIF elutes approximately in the 35% propanol gradient and IL-2 in the 40% well separated from each other. Exogenous IL-2 does not induce ISC in our assay and does not affect induction by BIF (Table IV). A role for endogenous IL-2 in the assay was excluded by the extensive depletion of T cells so that functional tests were negative (Table I), failure to detect IL-2 in culture supernates, and lack of effect of a monoclonal anti-IL-2 (Table IV). Factors which induce IgM and IgG secretion in human B cell lines (Maurer, et al. (1983) Supra, Teranishi, et al. (1982) Supra, Ralph, et al. (1983) Immunol. Lett. 7: 17; Saiki, et al. (1983) Eur. J. Immunol. 13: 31; Yoshizaki, et al. (1983) J. Immunol. 130: 1241) and human leukemic cells (Yoshizaki, et al. (1982) Supra) could also be separated from IL-2 by chromatography and by adsorption to B- or T-cell lines.

Other lymphokines which may act directly on B cells to promote humoral responses are B-cell growth factor (BGF) (Nakaniski (1983) J. Immunol. 130: 2219) and IL-1 (Hoffman, et al. (1980) Proc. Nat'l. Acad. Sci. U.S.A. 77: 1139). This system may include IL-1 since monocytes which produce IL-1 are a major cell type in the B-lymphocyte preparation. BGF could enhance numbers of ISC by promoting B-cell proliferation before differentiation to immunoglobulin secretion. The HPLC peak fraction of BIF is sometimes separated from the peak fraction of BGF activity. BGF was assayed by $^3$H-thymidine incorporation 3 days after addition to B cells which previously had been stimulated with suboptimally mitogenic concentration of Sac, as described by Muraguchi and Fauci [(1982) J. Immunol. 129: 1104]. Sac alone is a powerful mitogen for B cells in our system, but further experiments are required to determine if BGF can be routinely separated from BIF and whether BGF allows additional ISC to be generated.

Adsorption experiments suggest that IgM and IgG cell lines have surface receptors for BIF but that T and pre-B cell lines do not l(Yoshizaki, et al. (1982), Saiki et. al. (1983) Eur. J. Immunol. 13: 31). In view of the evidence in rabbits that anti-immunoglobulin induced acceptors on B cells for T cell-derived helper factors (Kishimoto, et al. (1975) J. Immunol. 115: 1179), we may expect that resting B cells do not express a receptor for BIF until stimulated into proliferation by Sac, specific antigen, or by other means.

The purification of BIF and suitable assays of the invention for monitoring BIF production will further our understanding of the regulation of humoral immunity and may aid in patient management in a variety of T-cell dysfunction syndromes, as well as immunodeficiency syndromes such as acquired immunodeficiency syndrome (AIDS), combined immunodeficiency syndrome, immunodeficiency caused by cancer treatments or exposure to radiation or immunodeficiency in elderly persons. Treatment may be effected with BIF or mixtures of BIF and BGF.

Stimulation of ISC in IgG cell line ARH-77 by LK or PMA

This disclosure is in Maurer, et al. (1983) Cell. Immunol. 79: 36 which is hereby incorporated by reference. A cell line assay for IgM-BIF is shown and cell lines positive and negative for receptors for this activity are described (Saiki, et al. (1983) Eur. J. Immunol. 13: 31). It is herein reported an IgG cell line which is greatly stimulated by PMA and lymphokine (LK) to generate ISC. The relation between PMA and BIF could now be examined. The results show that PMA and BIF act synergistically on the IgG line ARH-77, and suggest that IgM- and IgG-BIF may be distinct factors.

In screening a number of human B cell lines, ARH-77 showed the greatest response to PMA and LK. Stimulation of ISC by LK prepared from human spleen mononuclear cells reached a plateau at 20% v/v. PMA stimulation of ISC was optimal at 0.2 to 1 micrograms/ml. Several experiments examine the time course of ISC stimulation in ARH-77 cultures by PMA or LK. In most experiments PMA and LK caused large increases ISC levels at Days 2 and 3 of incubation. In agreement with previous observations (Ralph, et al. (1981) J. Clin. Investig. 68: 1093), stimulation of ISC in ARH-77 cultures by PMA generally correlated with growth inhibition of the cell line. ISC stimulation by LK was not accompanied by significant growth inhibition. With either agent viability remained greater than 85%.

In 17 experiments, ISC levels in PMA-treated cultures of ARH-77 exceeded those in corresponding unstimulated cultures by an average of 11-fold (Table V). In 18 experiments, ISC levels in LK-treated cultures of ARH-77 exceeded control levels by an average of 3.4-fold. In no instance was a new isotype of secreted immunoglobulin detected in cell lines treated with PMA or LK (Table VI). In order to examine the question of whether PMA and LK augment ISC levels by the same or independent mechanisms, the agents are used together. Table VII gives the result of four experiments in which optimal concentrations of PMA or LK or both were added to ARH-77 cultures and ISC assayed on Day 2 or 3. Additive or superadditive effects of dual stimulation were seen in every experiment suggesting that PMA and LK acted independently to increase ISC levels.

Peripheral blood lymphokine was concentrated by precipitation at 80% saturated ammonium sulfate and chromatographed on DE-52 cellulose. The material not binding to the ion-exchange column was enriched in BIF-stimulating ISC formation in ARH-77. This material was size fractionated on an AcA 44 Ultrogel column. Fractions which elute from the column slightly later than IL-2 contained BIF for the IgG line, with an apparent $M_r$ of 15,000 to 20,000. In addition, high-molecular-weight material also stimulated IgG secretion. In contrast, LK, which stimulated IgM secretion in the SKW6.4 line (Saiki, et al. (1983) Eur. J. Immunol. 13: 31)., was found only in the low-molecular-weight fraction. Chromatography of the low-molecular-weight fraction on blue agarose allowed a further separation of IgG-BIF activity from IL-2. The low-molecular-weight BIF stimulated similar numbers of ISC in ARH-77 as did unfractionated LK, suggesting that the purified factor has all the secretion-promoting activity present in LK.

Previous studies have shown that human B-lymphocyte cell lines may be stimulated to higher levels of immunoglobulin secretion by T cells (Kishimoto (1978) Supra; Kempner (1980) Supra), lymphokine factors (Muraguchi, et al. (1981) Supra; Teranishi (1982) Supra, Saiki, et al. (1983) Eur. J. Immunol., 13: 31), and by the tumor promoter PMA (Ralph, et al. (1981) J. Clin. Investig. 68: 1093). PMA induces ISC in peripheral blood mononuclear cells, but this effect is T-cell-dependent and appears to operate by stimulating production of T-cell replacing factors (Ralph, et al. (1981) Clin. Immunol. Immunopathol. 22: 340). With B-cell lines PMA stimulation occurs in the absence of T cells, and its additive effect with LK in the ARH line suggests that stimulation of B-cell lines by PMA is different from induction of blood B cells by PMA or by T-cell factors. Stimulation of cell line Ig secretion by PMA is unlikely to be due simply to growth inhibition since other growth-inhibiting conditions (serum derivation or thymidine block) do not induce ISC.

A phorbol ester binding assay was also developed to analyze the relative between PMA and LK. [$^3$H]Phorbol dibutyrate was used to avoid the nonspecific, hydrophobic binding of PMA (Sando, et al. (1981) J. Immunol. 78: 1139). Approximately $5 \times 10^5$ binding sites per ARH-77 cell were detected at saturation conditions (2 hr, 4° C., serum free, input 10 picomol/$10^6$ cells). Binding was inhibited by PMA and unlabeled phorbol dibutyrate, but not by LK. This indicates that PMA and LK do not share binding sites on ARH, and further supports the thesis that the two kinds of stimuli have independent effects on IgG secretion by ARH cells.

The factors that stimulate IgG secretion in the ARH-77 cell line were about 20,000 Mr, slightly smaller than IL-2 induced by PHA. In addition, a high-molecular-weight IgG-stimulating activity was seen. Teranishi, et al. (1982) Supra reported that BIF for a different IgG cell line had molecular weights of about 22,000 and 36,000. We previously showed that 20K BIF induces IgM, IgG, and IgA secretion in peripheral blood B cells activated by Staphylococcus bacteria (Saiki, et al. (1982) Proc. Nat'l. Acad. Sci. U.S.A. 79: 6008), and greatly stimulates IgM secretion in SKW6.4 cell (Saiki, et al. (1983) Eur. J. Immunol. 13: 31). However, the high-molecular-weight component which stimulated IgG secretion by ARH-77 did not induce IgM-ISC in Staphylococcus-activated blood B cells or in the SKW6.4 line. This suggests that some IgG-BIF are distinct from IgM-BIF. Therefore, the IgG lines may be more advanced in the plasmacyte differentiation pathway than blood B cells stimulated in culture, and able to respond to a late-acting high-molecular-weight BIF, or the high-molecular-weight LK may be a nonphysiological trigger for the IgG lines. Different factors for induction of IgM and IgG production in murine B cells have been implied by Isakson, et al. (1982) J. Immunol. 129: 2420. This is a new assay method for BIF using ARH-77 cells with and without the presence of mitogens.

BIF sensitive IgM cell line SKW6.4; clonal differences in B cells

A number of human B lymphoblast cell lines were tested to find a suitable model for induction of ISC by T cell replacing actor for use in analysis of B cell differentiation. Three clones derived from IgM line SKW6 show high levels of BIF stimulated secretion when stimulated with partially purified BIF size fractionated from conditioned medium of irradiated (1000 rads) human spleen cells stimulated with PWM. Irradiated cells were cultured at $2 \times 10^6$/ml in 1% FCS with 0.25% PWM for 2 days. The supernatant was concentrated 10 fold by amicon pressure filtration and material precipitating between 33 and 80% (v/v) ammonuim sulfate was applied to a Sephadex G-100 column. 15,000–30,000 MW BIF was used. 1 ml BIF was incubated with $5 \times 10^6$ cells for 4 hr. at 37° or 4° C. The three clones correspond to nonresponding, responding and high rate secreting B cells serving as basic models for analysis of B cell receptors for BIF and biochemical effects of BIF during B cell differentiation. This work is found in a recently published paper which is hereby incorporated by reference, Saiki, et al. (1983) Eur. J. Immunol. 13: 31.

Line SKW6 was cloned. Thirty-four clones were obtained which differed greatly in spontaneous and TRF (BIF)-induced levels of ISC. Certain clones were selected for further study. Clone 11 had a low background and almost no response to TRF: clone 4 had a low background and high response to TRF for IgM secretion; clone 3 had a high background and a good response to TRF; and clone 8 had the highest background and showed little stimulation of ISC by TRF.

Subcloning was performed after 3–5 weeks to obtain widely different clones and to determine the purity and stability of the clones. With low secretor clone 11, all 14 subclones obtained few or no ISC and had poor responses to TRF, if any, showing that this clone is quite stable and homogeneous. Of 16 subclones obtained from high secreting clone 8, 15 had relatively high levels of ISC which were not increased more than 2-fold by TRF. The prototype of this class was clone 8-6 with the highest numbers of ISC without TRF, about 6%. Further subcloning of clone 8-6 did not produce lines with higher Ig secretion. Subclones of clone 3 were generally similar to their parent, with 3-5 and 3-8 giving the highest numbers of ISC in the presence of TRF (14% of recovered cells). Most subclones of clone 4 were similar to their parent, with very low backgrounds and high responsiveness to TRF. Clones typical of three types of behavior, low-low (clone 11-2), low-high (4), and high-low (8-6) in background ISC and response to TRF were selected for further analysis.

Clone 4 cells were cultured in varying concentrations of TRF and the numbers of ISC at day 3 determined. ISC levels increased with TRF concentrations up to 20%, reaching a plateau in Ig secretion at higher amounts. TRF had no effect on cell division (doubling time about 23 h). To give just sufficient signals for optimal stimulation, a 20% TRF preparation was used in the remaining experiments. TRF had not effect on the high rate secretion by clone 8-6 or low secretion by clone 11-12. In clone 4, absolute numbers of ISC increased 30-fold by day 1 and thereafter increased in parallel with the total cell population for another 4 days. Attempts were made to determine whether the activity in this partially purified lymphokine preparation reflects a TRF which can replace the function of T cells for induction of ISC in normal B cells. Purified B cells from normal peripheral blood were cultured 6 days with T (PWM) or B cell (Cowan I) mitogens. T cells, TRF, or mitogen alone could not induce any ISC in purified B cells. However, in the presence of Cowan I, TRF could induce ISC at the same level as T-cells plus PWM (1% of initial B cells) and at about ¼ the level of T cell stimulation in the presence of both PWM and Cowan I (Table VIII). TRF at 10% (v/v) was optimal in induction of normal B cell ISC in the presence of Cowan I (1.3% of initial B cells). This partially purified TRF has similar efficiency and titration as crude PWM- and PHA-induced factors in inducing ISC in normal B cells.

Further experiments were designed to determine if TRF activity for normal B cells could be adsorbed by the different cell line clones. TRF was incubated with the 4 typical clones and pre-B cell line NALM-6 (Ralph, Immunol. Rev. (1979) 48: 107) at 4° C. and 37° C., respectively, for 4 hr. and its helper activity to induce ISC in both normal B cells and the cell line were compared. Both TRF functions were adsorbed by clone 4 but not by the pre-B line at 4° C. (Table IX) and 37° C. These results indicate the possibility that TRF helper molecules for normal B cells and the B cell line are identical, and that the cell line is a good model for normal B cell induction. Surprisingly, TRF-insensitive clones 8 and 11 also adsorbed most of the TRF activity, suggesting that these clones have TRF receptors on their surface but cannot properly transmit TRF signals intracellularly.

We found clonal differences in sensitivity of TRF for stimulation of Ig secretion within the same cell line. We also provide evidence that TRF molecules for both normal B cell differentiatino to secrete Ig and for the induction of IgM secretion in the cell line may be identical. In this study the Ig class was IgM, not IgG, the phenomenon was long-lived [more than 10 days with single stimulation] rather than transient (3 days), and the magnitude of stimulation was 20- to 30-fold rather 3- to 4-fold as reported previously [Muraguchi, et al. (1981) J. Immunol. 127: 412, 12]. These improved results were obtained by screening for a B cell line clone (clone 4) that had low background secretion but was very responsive to induction.

It is a common observation that not every cell is an ISC in human Ig-secreting clones [Muraguchi, et al. (1981) J. Immunol. 127: 412; Takahash (1969) J. Immunol. 102: 1388; Ralph, et al. (1981) J. Clin. Invest. 68: 1093). Usually less than 10% of cells are detected as ISC even in plasmacytoma-like lines [Ralph, et al. (1981) Supra], suggesting heterogeneity even within the same cell line clone. However, Miki, et al. [Miki, et al. (1982) J. Immunol. 128: 675] were able to use the line CESS to show that cells were sensitive to lymphokine signals only when they were in $G_1$ phase, and that augmentation of IgG production involved a stimulus-activatable serine esterase.

One reason for the heterogeneity in cell lines is that two or more different clones may coexist in the cell line since initiation to culture (Takahashi (1969) J. Immunol. 102: 1388). Another reason may be that different clones may be generated by somatic mutation during long-term culture. The best approach to this problem is the analysis of clones. Great variation was seen among the initial clones of line SKW6 in numbers of IgG secretors and inducibility. Subcloning after 3-5 weeks showed that the initial clones were fairly homogeneous but variants could still be detected. Thus, somatic mutation or variation may partly explain the clonal differences in this line. No homogeneously secreting or totally TRF-responding clones were found. The highest spontaneously secreting clone showed about 6% ISC (clone 8-6), and this was not improved by further subcloning. Ig is not secreted during mitosis (Buell, et al. (1968) Science 164: 1524). However, most cells in a randomly growing population are not in mitosis so this cannot explain why only 6% of cells are secreting in a freshly isolated cell line clone. Clones, 3, 4, 8 and 11 and parent SKW6 were similar in having low or undetectable levels of Fc and complement receptors as measured by red blood cell rosette assays. In addition, these cells all had the same HLA-DR antigens (D. Maurer, personal communication), making it very unlikely that any of the clones was a contaminant of a different cell line.

The humoral response to most antigens probably requires signals through the B cell Ig receptor (Ditton, R. W. (1975) Transplant Rev. 23: 66) and T cell signals. Mitogens are often used as the first signal, such as anti-Ig in rabbits [Kishimoto, et al. (1975) J. Immunol. 115: 1179) and mice (Parker, et al. (1980) J. Exp. Med. 152: 138), or Cowan I conditions described in humans (Saiki, et al. (1981) J. Immunol. 127: 1044) for studying induction of Ig secretion. It is believed that clone 4 represents B cells already stimulated by the first kind of signal, as with blood B cells stimulated by Cowan I and able to respond to TRF. Clone 11-2 failed to respond to TRF although it appeared by adsorption assay to have TRF receptors (Table IX). Therefore, it may be, like unstimulated normal B cells, unresponsive to TRF, or the clone may be defective in transmitting TRF signals intracellularly. Clone 8-6 is already secreting Ig at a relatively high rate and therefore similar to a plasma cell. These clones will provide a good model for investigation of the dynamics of TRF induction of humoral immunity at the cellular and genetic levels.

Analysis of IgM and IgG Secretion in human B cells, BIF and Phorbol Ester

Human B-cell lines were screened for stimulation of immunoglobulin production by incubation with lymphokine (LK) or tumor promoter, phorbol myristic acetate (PMA). One group of lines had essentially no immunoglobulin-secreting cells (ISC) under any condition (less than 0.01%), detected a reverse plaque assay. Another group of lines had high levels of ISC (greater than 5%) which was not increased substantially by inducing agents. In a third group of IgM and IgG lines, there were intermediate levels of ISC which could be increased by LK, PMA or both agents. No evidence for isotype switching in a number of stimulated IgM and IgG cell lines was detected. Clone SKW6.4 of an IgM line was highly responsive to a B-cell inducing factor (BIF) in LK. BIF for SKW6.4 and IgG line ARH-77 was weakly binding to DEAE cellulose, about 20,000 mol. wt. and separable from IL-2 by blue agarose chromatography. IL-2 did not stimulate secretion in SKW6.4 with or without purified BIF. In clone SKW6.4, BIF stimulated ISC per recovered cell up to 30-fold by day 1 of culture, and these plateau levels of about 6% ISC were maintained for longer than 4 days. Treatment of cells with BIF for less than 1 day was sufficient to produce maximum effect on this clone for the succeeding 4 days. Cells stimulated with BIF and then subcultured at day 3 without BIF showed ISC numbers increasing but at a slower rate than the total population, suggesting that the induced differentiation state is long-lived (half-life of ISC is greater than 6 days) and that ISC produce some daughter ISC. In declining cultures readdition of BIF boosted ISC levels again to about 6%. The continual presence of 20K BIF for 12 days had no apparent effect on total cell growth. In conclusion, a number of cell lines are sensitive to stimulation of immunoglobulin secretion and may provide models for induction of human antibody production.

Certain human B-lymphocyte lines in long-term culture can be stimulated to produce IgM or IgG by co-culture with normal allogeneic T-lymphocytes [Kishimoto, et al. (1978) Nature (London) 271: 756, Kempner, et al. (1980) Cell. Immunol. 55: 32] by incubation with lymphokine (LK) preparations (Muraguchi, et al. (1981) J. Immunol. 127: 412; Teranishi, et al. (1982) J. Immunol. 128: 1903; Saiki, et al. (1983) Eur. J. Immunol. 13: 31], and by incubation with tumor promoter, phorbol myristic acetate (PMA) [Ralph, et al. (1981) J. Clin. Investig. 68:1093]. We have screened a number of B-lines for stimulation of immunoglobulin-secreting cells (ISC) by LK or PMA to determine how general is the sensitivity of cell lines to inducing signals. THe B-cell-inducing factor (BIF) has been partially purified and shown not to involve IL-2. In one clone which is greatly stimulated by BIF, the effect of ISC induction on cell proliferation and maintenance of secreting cells was studied.

Cell lines are described in Table X. All contain Epstein-Barr virus (EBV) (G. Klein and K. Nilsson, personal communications) and are presumably derived from normal B-lymphocytes, except for EBV-negative pre-B-lymphoma, NALM-6, and B-lymphomas, Bjab and U-698, and EBV-infected Bja/HRH. Cultures were grown in RPMI 1640 medium containing 10% fetal bovine serum.

BIF was purified through the red agarose step above.

A number of human B-cell lines were screened for immunoglobulin-secreting cells (ISC) and resonse to LK and PMA, using a reverse plaque assay. LK was two-day conditioned medium of human spleen cells stimulated with PHA. PHA alone had no effect on the B-cell lines. Table X shows that pre-B line, NALM-6, lymphoma line, Bjab, and clone. SKW6.11-2, had no detectable ISC and could not be induced to secrete immunoglobulin by Lk or PMA. Another group of lines had high constitutive levels of ISC with little or no stimulation by LK or PMA. These two groups of B-cell lines were not studied further. A third group of lines had low levels of ISC and were stimulated to various extents by incubation with LK or PMA. Table X shows the results for the optimal day of incubation (usually day 2 or 3) and concentration of PMA, which varied from 0.05 to 1 microgram/ml depending on the line. Clone SKW6.4 was the most sensitive to LK stimulation of IgM secretion, and ARH-77 was the most sensitive IgG line to ISC induction by LK and PMA. It is likely that other lines which are only weakly stimulated by LK contain highly responsive subsets of cells which can be cloned out of the parent culture as for the clone SKW6.4

LK at 20% v/v gave optimal stimulation of SKW6.4 and ARH-77, and BIF contained in a 20,000 mol. wt. fraction of blood LK stimulated similar numbers of ISC as crude LK. This indicates that the 20K BIF, in comparison to the unfractionated LK, contains all the activity necessary for ISC formation with these two cell lines. Upon size fractionation of LK from peripheral blood cells stimulated with PHA, BIF for SKW6.4 and ARH-77 partially overlapped with 26,000 mol. wt. IL-2 (T-cell growth factor). BIF could be separated from 11-2 by affinity chromatography on blue agarose. Purified IL-2 did not stimulate immunoglobulin secretion by the cell lines, and the activity of the BIF preparation which was free of IL-2 was not enhanced by addition of IL-2 (Table XI).

The SKW6.4 clone which is strongly stimulated by LK was analyzed for growth and maintenance of secreting cells in the presence of LK. Absolute numbers of ISC increased 30-fold by day 1 and thereafter increased exponentially in the presence of BIF. Expressed per recovered cell, ISC levels increased to about 6% by day 1, after which the ratio remained constant up to 4 days of culture. BIF did not have any significant effect on overall cell growth. Another clone SKW6.8-6 had a high constitutive levels of ISC which did not change in the presence of BIF. Clone SKW6.11-2 was not sensitive to BIF and did not produce any ISC at any day tested.

Further experiments were performed to determine low long BIF should be present to stimulate clone 4. One day co-culture with BIF followed by washing provided the same stimulation during the subsequent 3 days as untouched BIF cultures. Since BIF was used at just optimum concentrations, there probably was little new induction of ISC from non-secreting cells after the first day. These results suggest that most of the responding cells were induced in 24 hr. and that the continued increase in absolute numbers of ISC in subsequent days, at the same rate as total cell numbers, was due to induced ISC dividing with the general population and producing Ig-secreting daughter cells by cell division. However, some factors must limit the differentiated state since high percentages of ISC were not found during cloning of induced cells.

In order to determine how permanent was the signal provided by BIF, longer-term cultures were examined. Clone 4 cells were incubated with BIF and then washed and subcultured with or without BIF at day 3 or 8. After 4 days in culture without BIF, ISC numbers increased at a slower rate than the total cell population. Thus, the present ISC declined slowly (half-life more than 6 days), showing that the induced differentiation state was long-lived but either not permanent or diluted out by faster growing non-secretors. Addition of more BIF on day 3 after washing did not increase ISC levels further in this subline, but maintained them at 6% for another 5 days. In declining cultures re-addition of BIF on day 8 boosted the ISC rate againt to about 6%. During the culture, cell viability was more than 95% and growth was unaffected by BIF. These results suggest that some cells return to an unstimulated state during the long-term culture, but they (or other cells) are sensitive to additional BIF as seen in the original population.

This study examined B-cell line responses to two stimuli, LK and PMA. The results show that lines lacking detectable ISC could not be induced to secrete immunoglobulin. However, among lines with moderate constitutive secretion (0.007–1.1% ISC), more than half showed greater than 3-fold stimulation by one or both agents. In certain lines 30 stimulation of ISC by LK and 40-fold by PMA could occasionally be obtained (Table X). However, the highest level of induced secreting cells never exceeded 10% of the total population despite repeated cloning.

PMA induces ISC in peripheral blood mononuclear cells, but this effect is T-cell dependent and appears to operate by stimulating production of T-cell-replacing factors (Ralph, et al. (1982) J. Immunol. Immunopathol. 25:114). With B-cell lines PMA stimulation occurs in the absence of T-cells, and its additive effect with LK and independent binding sites in the ARH line suggests that stimulation of B-cells lines by PMA is different from induction of blood B-cells by PMA or by T-cell factors.

We previously showed tht BIF of 20,000 mol. wt. purified from LK induced IgM, IgG and IgA secretion in human peripheral blood B-cells activated by Staphylococcus bacteria (Saiki, et al. (1982) Proc. Nat'l. Acad. Sci. U.S.A. 79: 6008). This fraction also stimulated IgM-ISC in line SKW6.4 and IgG-ISC in ARH-77 (Maurer, et al. (1983) Cell. Immunol. 79: 36), as described by Teranishi, et al. [(1982) J. Immunol. 128: 1903] and Muraguchi, et al. [(1981) J. Immunol. 127: 412] for other IgG cell lines. BIF for the cell lines could be separated from IL-2 by affinity chromatography on blue agarose, isoelectric focusing and preferential adsorption to B-cells. Table XI shows that BIF stimulation of ISC in cell lines is independent of IL-2 since IL-2 has no effect on the lines with or without BIF. A higher molecular weight LK also stimulated IgG-ISC in ARH-77 [Maurer, Supra] and another cell lines [Teranishi, Supra], but not in peripheral blood cells or the IgM line SKW6.4.

In the clone SKW6.4, BIF stimulation of ISC was long-lived (greater than 10 days with a single stimulus), with no apparent effect on cell growth. Other clones of the same parent line were found which secreted at a high rate and could not be stimulated by BIF (clone 8-6) or which had undetectable ISC with or without BIF (clone 11-2). All 3 clones apparently have receptors for BIF as indicated by adsorption experiments [Saiki, et al. (1983) Eur. J. Immunol. 13: 31]. It is likely that cell lines will continue to be valuable models for regulation of human antibody production.

TABLE I

Assay for BIF Using Normal Donors on Different Days

| Donor | Sac + BIF ISC/2 × 10⁴ cells | Control | Sac % Maximum | Sac + PWM |
|---|---|---|---|---|
| 1 | 902 | 0.7 | 2.9 | 2.2 |
|   | 170* | 11.2 | 36.5* | 12.4 |
|   | 235 | 7.7 | 12.3 | 8.5 |
|   | 326 | 1.8 | 2.4 | 4.9 |
| 2 | 468 | 0.9 | 4.9 | 7.4 |
|   | 1015 | 3.0 | 14.5 | 18.2 |
|   | 1800 | 2.7 | 5.6 | 3.1 |
|   | 520 | 1.9 | 9.4 | ND |
| 3 | 1020 | 0.1 | 2.2 | 8.8 |
|   | 552 | 3.0 | 7.2 | 6.9 |
|   | 1752 | 1.5 | 2.5 | 3.0 |
| 4 | 2000 | 0.4 | 8.0 | 7.0 |
|   | 1136 | 1.7 | 3.0 | ND |
| 5 | 826 | 2.8 | 4.6 | 5.7 |
|   | 1010 | 1.2 | 7.4 | ND |
|   | 665 | 2.2 | 5.0 | 4.4 |
| 6 | 356 | 1.1 | 4.2 | 8.7 |
| 7 | 2000 | 0.6 | 0.9 | 1.1 |
|   | 1062 | 1.0 | 7.8 | 9.5 |
|   | 489 | 1.2 | 3.3 | 2.9 |
| 8 | 965 | 6.9 | 13.5 | 11.6 |
| 9 | 1297 | 0.6 | 2.9 | 3.6 |

T cells were depleted from donor blood mononuclear cells by two cycles of E rosetting and the resultant B-cell population was incubated with Sac plus optimum amounts of BIF as described. After 6 or 7 days, total ISC per 2 × 10⁴ initial cells were measured. Incubations with no stimulus (control), Sac, and Sac plus PWM were similarly assayed and are shown as percent of (Sac plus BIF). Each line represents a separate blood sample collected on a different day showing the variation in donor response and/or experimental assay.
ND, not done.
*BIF assay invalid due to poor stimulation above values for Sac alone.

TABLE II

Purification of BIF

| Fraction | Total protein mg | Total activity U | Sp act U/mg protein | Purification -fold | Yield % |
|---|---|---|---|---|---|
| I Lymphokine | 10,800 | 150,000* | 14* | 1 | 100 |
| II (NH₄)₂SO₄ precipitate | 9,000 | NT | NT | | |
| III DE-52, 0.1 M | 135 | 72,000* | 533* | 38 | 48 |
| 0.3 M | | <6,000 | | | |
| 0.5 M | | 15,000 | | | |
| IV 20,000 M_r | 78 | 41,600 | 520 | 37 | 28 |
| V Blue agarose | 2.3 | 7,600 | 3,304 | 236 | 5 |
| VI Red agarose | 0.41 | 5,940 | 14,490 | 1,035 | 4 |
| VII HPLC | 0.0042 | 650 | 154,800 | 11,050 | 0.4 |

Footnote to Table II
Three liters of lymphokine was prepared in 0.25% bovine serum albumin and the proteins concentrated by precipitation with 80% saturated ammonium sulfate. The precipitate was dialyzed and applied to a DEAE cellulose (DE-52). Protein was batch-eluted at 0.1 M, 0.3 M and 0.5 M naCl, 0.05 M Tris-HCl, pH 7.8. The first fraction from the DE-52 column was concentrated and size-fractionated on an AcA 44 ultrogel column. Proteins of between 15K and 25K apparent molecular mass (M_r) were pooled and applied to a blue agarose column (step IV). High salt eluates were pooled, dialyzed against PBS and loaded on a 10 ml Procion-red agarose column. The high salt eluates containing both IL-2 (Welte, et al. (1982) J. Exp. Med. Supra) and BIF were then fractionated by reverse phase HPLC. Purification step VII in the Table is HPLC fraction 28 which is free of IL-2. Protein was estimated by Bio-Rad Protein Assay (microassay procedure using bovine albumin as a standard).
*Activity may be higher than shown since titration curve does not reach the plateau level due to inhibitory substances.

TABLE III

Co—Purification of BIF for IgM, IgG and IgA Production

| Preparation | IgM | Induced ISC IgG | IgA |
|---|---|---|---|
| Lymphokine | 160 ± 7 | 152 ± 17 | 72 ± 4 |
| DE-52, 0.1 M | 169 ± 7 | 171 ± 7 | 67 ± 7 |
| DE-52, 0.5 M | 46 ± 8 | 41 ± 5 | 19 ± 1 |
| 20,000 $M_r$ | 103 ± 6 | 92 ± 12 | 47 ± 14 |
| Blue Agarose, 0.8 M | 184 ± 25 | 136 ± 21 | 68 ± 17 |

Legend to Table III:
Lymphokine, the 0.1 M and 0.5 M NaCl fractions of DE-52 chromatography (Table II) the peak size fraction from the Ultrogel column (20,000 $M_r$) and blue agarose fraction free of IL-2 (0.8 M NaCl eluate) were added at 20 microliters to cultures of B cells + SAC. Class-specific ISC were detected as above.

Background values with SAC alone were substracted.

TABLE IV

Independence of BIF Action From IL-2

| | Induced ISC | | |
|---|---|---|---|
| | 0 | BIF | BIF (1:8) |
| No addition | 0 | 868 ± 42 | 207 ± 22 |
| + IL-2 | 0 | 830 ± 16 | 219 ± 13 |
| + anti-IL-2 | 0 | 821 ± 51 | 245 ± 18 |

ISC were induced in Sac-stimulated B cells by Fraction V BIF (blue agarose purification, 0.8 M NaCl, containing less than 5 U/ml IL-2, or 1:8 dilution. Parallel incubations included 20% Fraction VI IL-2 (red agarose purification step, below* 100 U/ml) or 100 neutralizing units of monoclonal antibody to IL-2. The number of ISC in B-cell cultures with Sac alone, 38 ± 2, was subtracted. IL-2 was free of BIF activity and did not enhance optimal or suboptimal concentrations of BIF.
*Welte, et al. (1982) Supra.

TABLE V

Stimulation of ISC in Human IgG Cell Line ARH-77 by LK and PMA

| | ISC per $10^4$ recovered cells incubated with | | Stimulation index[a] | |
|---|---|---|---|---|
| Control | LK | PMA | LK | PMA |
| .3 ± 0.4 | 21 ± 0.4 | 67 ± 20 | 7.0(1.5–8.7) n = 18 | 22.3(2.7–42) n = 17 |

Legend for Table V:
Note: Cells were incubated 2 or 3 days with 20% LK or 0.1–1 microgram/ml PMA, washed, and assayed for ISC per $10^4$ recovered cells. Typical data are shown for one experiment.
[a]Stimulation index = (experimental/control). Range of stimulation indices in parentheses and total number (n) of experiments is also shown.

TABLE VI

Constancy of Immunoglobulin Isotype during Stimulation

| Line | Inducing agent | ISC per $10^4$ Cells IgM | IgG | SI[a] | IgA |
|---|---|---|---|---|---|
| ARH-77 | 0 | | —[b] | | 9 ± 1 |
| | LK | | 51 ± 3 | 5.7 | |
| | PMA | | 44 ± 9 | 4.9 | |
| BM.B | 0 | 490 ± 10 | — | | — |
| DAKIKI | 0 | — | | | 88 ± 7 |

Note: Cells incubated 3 days with 0 or 20% LK or 0.2 ug/ml PMA and assayed for ISC using class-specific developing antisera (Saiki, et al. (1981) J. Immunol. 127:1044).
[a]Stimulation index.
[b]Less than 0.1.

TABLE VII

Additive Effects of PMA and LK on ARH-77 Immunoglobulin Secretion

| Experiment | Day | Stimulation of ISC (Stimulation index) | | |
|---|---|---|---|---|
| | | PMA | LK | PMA + LK |
| 1 | 2 | 2.6 | 3.0 | 10.0 |
| | 3 | 22.3 | 7.0 | 29.3 |
| 2 | 2 | 9.1 | 4.3 | 13.3 |
| | 3 | 41.9 | 8.7 | 50.0 |
| 3 | 2 | 8.5 | 3.0 | 6.1 |
| | 3 | 35.0 | 4.6 | 65.7 |
| 4 | 2 | 3.1 | 2.0 | 4.8 |

Note: Data of four consecutive experiments on stimulation of ISC by 2 or 3 days' treatment with 0.2 micrograms/ml PMA, 20% LK or both, as in Table V.

TABLE VIII

Comparison of helper activity of T cells and TRF (BIF) on induction of ISC from normal B cells[a]

| Concentration of TRF (%) | Without | With |
|---|---|---|
| | Cowan I | |
| 0 | 0 | 0 |
| 5 | 0 | 97 ± 11 |
| 10 | 0 | 132 ± 14 |
| 20 | 0 | 117 ± 16 |
| No. of T cells + PWM $10^5$ | 96 ± 18 | 471 ± 43 |

[a]Normal B cells ($10^5$) were cultured with additions as shown and ISC were detected by reverse hemolytic plaque assay on day 6 and expressed per $10^4$ initial B cells, as described (Saiki, et al. (1983) Eur. J. Immunol., 13:31.

TABLE IX

Adsorption of TRF for both normal and cultured B cells by cell line clones[a]

| Stimulus | Normal B cell ISC (%) | Clone 4 ISC (%) |
|---|---|---|
| None | 0 | 22 ± 4 |
| TRF | 113 ± 12 (100) | 425 ± 21 (100)[b] |
| TRF adsorbed by | | |
| Clone 3-8 | 23 ± 4 (20) | 141 ± 16 (29) |
| Clone 4 | 15 ± 2 (13) | 117 ± 14 (23) |
| Clone 8-6 | 6 ± 2 (5) | 47 ± 6 (6) |
| Clone 11-2 | 4 ± 1 (3) | 37 ± 5 (4) |
| Pre-B line Nalm 6 | 99 ± 16 (8) | 416 ± 23 (98) |
| Clone 11-2 does not suppress TRF induction of ISC | | |
| None | | 47 ± 6 |
| TRF | | 511 ± 58 |
| TRF + clone 11-2[c] | | 602 ± 73 |
| TRF + clone 11-2 alone[d] | | 15 ± 3 |

[a]Normal B cells were cultured 6 days with Cowan I and 10% TRF samples as in Table VIII. Clone 4 was incubated 3 days with TRF samples at 20%. IgM ISC were expressed per $10^4$ (normal B) or $10^3$ (clone 4) initial cells. TRF was adsorbed by a 4-h incubation with 5 × $10^6$ cells at 4° C. All clones of SKW6 adsorbed TRF for both normal B cells and clone 4. Loss of TRF activity by adsorption on nonresponding clone 11-2 was not due to inactivation of TRF or suppression of its effect. % of induced ISC.
[b]% of induced ISC.
[c]Five × $10^3$ clone 4 plus 5 × $10^3$ clone 11-2 cells per 0.2 ml incubation. ISC given per 2 × $10^4$ recovered cells (assuming that half the cells are clone 4 and that secretion by clone 11-2 is negligible).
[d]TRF plus $10^4$ clone 11-12 cells alone per 0.2 ml incubation.

TABLE X

Stimulation of ISC in human B-cell lines by LK and PMA

| B-cell line | Ref. | Isotype | ISC per 10 recovered cells incubated with: Control | I.K. | PMA | Stimulation index I.K. | PMA |
|---|---|---|---|---|---|---|---|
| (A) No ISC | | | | | | | |
| NAIM-6 | 10 | cμ[b] | 0 | 0 | 0 | 0. n = 2 | 0. n = 2 |
| Biab | 10 | IgM | 0 | 0 | 0 | 0. n = 2 | 0. n = 2 |

TABLE X-continued
Stimulation of ISC in human B-cell lines by LK and PMA

| | B-cell line | Ref. | Isotype | ISC per 10 recovered cells incubated with: Control | I.K. | PMA | Stimulation index I.K. | PMA |
|---|---|---|---|---|---|---|---|---|
| | SKW6.11-2 | 5 | IgM | 0 | 0 | 0 | 0. n = 7 | 0. n = 2 |
| (B) | High level | | | | | | | |
| | SB | 10 | IgM | 302 ± 17 | 588 ± 62 | 236 ± 19 | 1.9. n = 1 | 0.8. n = 1 |
| | U698 | 10 | IgM | >1000 | >1000 | >1000 | . n = 1 | . n = 1 |
| | BJA HRH | 11 | IgM | 789 ± 58 | >1000 | >1000 | . n = 1 | . n = 1 |
| | BM-NH | 6 | IgM | 262 ± 29 | 351 ± 11 | 607 ± 38 | 1.3(1.1 1.3)(n = 2) | 2.3(2.3 2.9)(n = 2) |
| | BM.B | 6 | IgM | 490 ± 10 | 190 ± 40 | 470 ± 10 | 0.7(0.4 1.0)(n = 3) | 1.0(0.6 3.0)(n = 4) |
| | SKW6.8-6 | 5 | IgM | 644 ± 22 | 654 ± 37 | 702 ± 61 | 1.0(1.0 1.1)(n = 2) | 1.1(1.0 1.1)(n = 2) |
| (C) | Low and inducible | | | | | | | |
| | RPMI 1788 | 6 | IgM | 32 ± 3 | 42 ± 6 | 49 ± 8 | 1.3(1.3 3.2)(n = 2) | 1.5(1 4.5)(n = 6) |
| | RPMI 1788.2 | 6 | IgM | 0.7 ± 0.1 | 0.9 ± 0.2 | 4.1 ± 2.1 | 1.3(0.9 2.3)(n = 3) | 5.9(4.2 9.0)(n = 3) |
| | SKW6 | 5 | IgM | 24 ± 3 | 36 ± 0 | 73 ± 7 | 1.5(1.2 5.5)(n = 5) | 3.0(1 4.9)(n = 6) |
| | SKW6.4 | 5 | IgM | 22 ± 4 | 425 ± 21 | 25 ± 2 | 16.3(5.1 35.5)(n = 16) | 1.2(0.8 2.0)(n = 3) |
| | BM.A | 6 | IgM | 7 ± 2 | 8 ± 1 | 20 ± 3 | 1.1(0.9 1.1)(n = 2) | 2.9(2.9 4.4)(n = 3) |
| | CESS | 3.12 | IgG | 110 ± 6 | 150 ± 27 | 200 ± 20 | 1.3(1.3 3.5)(n = 2) | 1.8(1 1.8)(n = 3) |
| | ARH-77 | 6 | IgG | 3 ± 0.4 | 21 ± 0.4 | 67 ± 20 | 7.0(1.5 8.7)(n = 18) | 22.3(2.7 42)(n = 17) |

Cells were incubated 2 or 3 days with 20% LK or 0.05 1 μg/ml PMA, washed and assayed for ISC per 10$^4$ recovered cells. Typical data are shown for one experiment.
$^a$Stimulation index = (experimental/control). Range of stimulation indices in parentheses and total number (n) of experiments is also shown.
$^b$Cytoplasmic μ-chains.

3. Muraguchi, A., Kishimoto, T., Miki, Y., Kuritani, T., Kaieda, T., Yoshizaki, K. and Yamamura, Y. (1981) J. Immunol. 127: 412-416.
5. Saiki, O. and Ralph, P. (1983) Eur. J. Immunol. 13: 31-34.
6. Ralph, P. and Kishimoto, T. (1981) J. Clin. Invest. 68: 1093-1096.
10. Ralph, P. (1979) Immunol. Rev. 48: 107-121.
11. Klein, G., Zeuthen, J., Terasaki, P., Billing, R., Honit, R., Jondal, M., Westman. A. and Clements, G. (1976) Int. J. Cancer 18: 639-649.
12. Bradley, T. P., Pilkington, G., Garson, M., Hodgson, G. S. and Kraft, N. (1982) Br. J. Haematol. 51: 595-604.

TABLE XI
Stimulation of ISC by BIF does not depend on IL-2

| Cell lines | 0 | IL-2 | 20% BIF | 20% BIF + IL-2 | 5% BIF | 5% BIF + IL-2 |
|---|---|---|---|---|---|---|
| SKW-6.4 | 56 ± 4 | 63 ± 14 (1.1) | 481 ± 61 (8.6) | 470 ± 28 (8.4) | 144 ± 19 (2.6) | 161 ± 18 (2.9) |
| ARH-77 | 18 ± 2 | 17 ± 1 (0.9) | 109 ± 17 (6.4) | 116 ± 20 (6.5) | 58 ± 15 (3.2) | 49 ± 12 (2.5) |

Cells were incubated with 20% Fraction VI IL-2 (red agarose purification step, 100 U ml) or 5 or 20% Fraction V BIF (blue agarose 0.8 M NaCl) and assayed for ISC Stimulation index is given in parentheses. Incubations with BIF were significantly different from controls but not different from BIF plus IL-2.

What is claimed:

1. Method for the purification of B-cell inducing factor (BIF) which comprises:
   (a) antigen-stimulation of human immunoregulatory cells to produce BIF;
   (b) recovery of BIF from culture medium;
   (c) contacting the recovered BIF with an ion exchanger;
   (d) size-fractionation of BIF active fractions from ion-exchange; and
   (e) agarose chromatography of BIF active fractions derived from gel chromatography.

2. Method of claim 1 wherein the BIF active fractions of step (e) are further purified by high pressure liquid chromatography.

3. Method of claim 1 wherein human immunoregulatory cells are stimulated by activators selected from the group consisting of *Staphylococcus aureus* strain Cowan I, lymphokine, PMA, PWM, PHA, Con A, staphylococcus Protein A, allogeneic T-cells and mixtures thereof.

4. Method of claim 2 wherein the high pressure liquid chromatography is reverse phase HPLC.

5. Purified human BIF.

6. BIF of claim 5 having a specific activity of approximately 154,000 U/Mg Protein.

7. BIF of claim 5 having a molecular weight of approximately 20,000 daltons.

8. BIF of claim 5 wherein said BIF stimulates production of immunoglobulins in B cells.

9. BIF of claim 8 wherein said BIF stimulates production of Immunoglobulins selected from the group consisting of IgM, IgG and IgA.

10. Purified human BIF obtained by the method of claim 1.

11. Purified human BIF obtained by the method of claim 2.

12. Purified human BIF essentially free of IL-2 activity.

13. Purified human BIF essentially free of Interferon activity.

14. Method for the purification of B-cell growth factor (BGF) which comprises:
   (a) antigen-stimulation of human immunoregulatory cells to produce BGF;
   (b) recovery of BGF from culture medium;
   (c) contacting the recovered BGF with an ion exchanger;
   (d) size-fractionation of BGF active fractions from ion-exchange; and
   (e) agarose chromatography of BGF active fractions derived from gel chromatography.

15. Method of claim 14 wherein the BGF active fractions of step e) are further purified by high pressure liquid chromatography.

* * * * *